(12) United States Patent
Tsuji (10) Patent No.: US 6,906,794 B2
(45) Date of Patent: Jun. 14, 2005

(54) SEMICONDUCTOR WAFER INSPECTION APPARATUS

(75) Inventor: Haruyuki Tsuji, Ina (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/438,561

(22) Filed: May 15, 2003

(65) Prior Publication Data

US 2003/0202178 A1 Oct. 30, 2003

Related U.S. Application Data

(63) Continuation of application No. PCT/JP02/09637, filed on Sep. 19, 2002.

(30) Foreign Application Priority Data

Sep. 19, 2001 (JP) ........................................ 2001-285637
May 28, 2002 (JP) ........................................ 2002-154183

(51) Int. Cl.[7] ............................................. G01N 21/88
(52) U.S. Cl. ................................. 356/237.4; 356/237.5
(58) Field of Search ................ 356/237.1, 237.2–237.5, 356/394, 614; 250/559.29, 559.36, 559.42; 382/141, 144–151; 348/86, 87, 126

(56) References Cited

U.S. PATENT DOCUMENTS 4,887,904 A * 12/1989 Nakazato et al. .......... 356/621
5,438,209 A * 8/1995 Yamamoto et al. ..... 250/559.29
5,684,599 A * 11/1997 Shimoyama et al. ....... 356/400
6,249,342 B1 * 6/2001 Cheng ...................... 356/237.2
6,576,919 B1 * 6/2003 Yoshida ..................... 250/548

FOREIGN PATENT DOCUMENTS

| EP | 1 001 460 A1 | 5/2000 |
|---|---|---|
| JP | 9-269298 A | 10/1997 |
| JP | 11-281337 A | 10/1999 |
| JP | 2000-46537 A | 2/2000 |
| JP | 2000-136916 A | 5/2000 |
| JP | 2000-174076 A | 6/2000 |

\* cited by examiner

Primary Examiner—Richard A. Rosenberger
Assistant Examiner—Vincent P. Barth
(74) Attorney, Agent, or Firm—Frishauf, Holtz, Goodman & Chick, P.C.

(57) ABSTRACT

A semiconductor wafer inspection apparatus is provided with a rotatable table on which a semiconductor wafer is held by suction, an illuminating device which illuminates at least an edge portion of the semiconductor wafer held on the rotatable table, an imaging device which captures an image of the edge portion of the semiconductor wafer when the edge portion is illuminated by the illuminating device, an image processing device which detects at least an edge cut amount or a crack by acquiring the image of the edge portion which is captured by the imaging device, and a display section which displays an image of the edge portion subjected to image processing by the image processing device.

5 Claims, 10 Drawing Sheets

| Identified defect | | X coordinate | Y coordinate | Area |
|---|---|---|---|---|
| Scratch | G2 | 32.5 | 94.6 | 2.36 |
| | G10 | −25.8 | 96.6 | 0.75 |
| | | | | |
| Dust | G3 | −78.6 | 61.8 | 1.63 |
| | G11 | 62.5 | −78.1 | 0.78 |
| | G12 | 19.5 | 98.1 | 0.25 |
| | | | | |
| Chipping | G1 | 45.7 | 88.9 | 1.56 |
| | G13 | −91.6 | 40.1 | 1.32 |
| | | | | |
| Abnormal edge cut | G4 | 15.8 | −98.7 | NG |
| | | | | |
| Others | G14 | 97.8 | −20.9 | 1.56 |
| | G15 | 84.7 | −53.2 | 0.75 |

SEMICONDUCTOR WAFER INSPECTION APPARATUS

CROSS-REFERENCE TO RELATED APPLICATIONS

This is a Continuation Application of PCT Application No. PCT/JP02/09637, filed Sep. 19, 2002, which was not published under PCT Article 21(2) in English.

This application claims the benefit of priority from prior Japanese Patent Application No. 2001-285637, filed Sep. 19, 2001, the entire contents of which are incorporated herein by reference.

BACKGROUND OF THE INVENTION

1. Field of the Invention

The present invention relates to a semiconductor wafer inspection apparatus which detects defects (including scratches, dust, and cracks) at the outer peripheral portion of a semiconductor wafer (hereinafter referred to as a "wafer edge portion."

2. Description of the Related Art

Normally, semiconductors are manufactured by executing steps described below, and defect inspection is executed in each manufacturing step. In the pre-process of semiconductor device manufacture, an oxide film ($SiO_2$) is formed on the surface of a semiconductor wafer (hereinafter referred to simply as a "wafer"), and then a thin silicon nitride film is deposited on the oxide film.

Then, a photolithography step is carried out to form a thin film of photoresist (photosensitive resin) on the surface of the semiconductor. Subsequently, an adequate amount of rinsing liquid is dropped onto the wafer edge portion of the wafer, and the photoresist is removed from the wafer edge portion of the wafer by an amount corresponding to a predetermined width.

Then, processing using an exposure device, such as a stepper, is executed. That is, ultraviolet rays are guided to the photoresist-coated wafer by way of a mask corresponding to a semiconductor circuit pattern, so that the semiconductor circuit pattern is transferred onto the photoresist. Then, developing is executed. For example, the exposed photoresist is dissolved in a solvent, thereby leaving the not exposed resist pattern.

Then, the oxide film and silicon nitride film formed on the surface of the wafer are successively subject to selective removal (etching), using the resist pattern remaining on the surface of the wafer as a mask. The resist pattern is then removed from the surface of the wafer by ashing (resist separation). The resultant wafer is cleaned of impurities.

In the semiconductor manufacturing process described above, defect inspection is carried out in each manufacturing step. In the defect inspection, the surface of the semiconductor wafer is mainly inspected to see if there are scratches, dust, cracks, stains or uneven portions. In recent years, the observation of the edge cut amount, the distribution, etc. of the wafer is required. In particular, it should be noted that cracks result in the breaking of the wafer itself. This being so, the presence or absence of cracks at the wafer edge portion has to be detected as early a step as possible to determine whether the wafer is good or bad.

A technique for inspecting a wafer edge portion is described, for example, in Jpn. Pat. Appln. KOKAI Publication No. 9-269298. According to this technique, a collimated beam condensed by an elliptic mirror is guided to the edge portion of a wafer. Of the diffracted light obtained thereby, the low-order components are shielded so that the elliptic mirror condenses high-order components of the diffracted light. On the basis of the intensity and/or the frequency components of the diffracted light, a defect at the wafer edge portion or the property of the wafer edge portion is identified. A technique for allowing a focal position to be located inside a wafer and enabling detection of diffused light coming from inside the wafer, is also known in the art, as seen in Jpn. Pat. Appln. KOKAI Publication No. 2000-46537. Furthermore, a technique for irradiating the edge portion of a wafer with an infrared laser beam and examining the wafer by means of at least one video camera by slanting the wafer relative to the laser beam, is also known in the art, as seen in Jpn. Pat. Appln. KOKAI Publication No. 2000-136916.

Although the techniques described above enable detection of the edge portion of a wafer, they in no way detect a defect at that wafer edge portion, especially an edge cut line width. For this reason, the processing in the steps that follow the formation of a thin photoresist film may give rise to a defective wafer or other undesirable results.

For defect inspection, image data (an edge image) on the entire outer circumference of a wafer has to be acquired. In the above technologies, however, the edge image of the entire circumference is not acquired, and the entire circumference of the wafer edge portion of a semiconductor wafer is not examined for defect detection.

An object of the present invention is to provide a semiconductor wafer inspection apparatus which can easily inspect the outer circumference of a semiconductor wafer in a short time in a semiconductor manufacture inspection process.

BRIEF SUMMARY OF THE INVENTION

A semiconductor wafer inspection apparatus of the present invention comprises: a rotatable table on which a semiconductor wafer is sucked and held; an illuminating device which illuminates at least the edge portion of the semiconductor wafer held on the rotatable table; an imaging device which captures an image of the edge portion of the semiconductor wafer when the edge portion is illuminated by the illuminating device; an image processing device which detects at least an edge cut amount or a crack by acquiring the image of the edge portion captured by the imaging device; and a display section which displays an image of the edge portion subjected to image processing by the image processing device.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will now be described with reference to the accompanying drawings.

Figure 1:
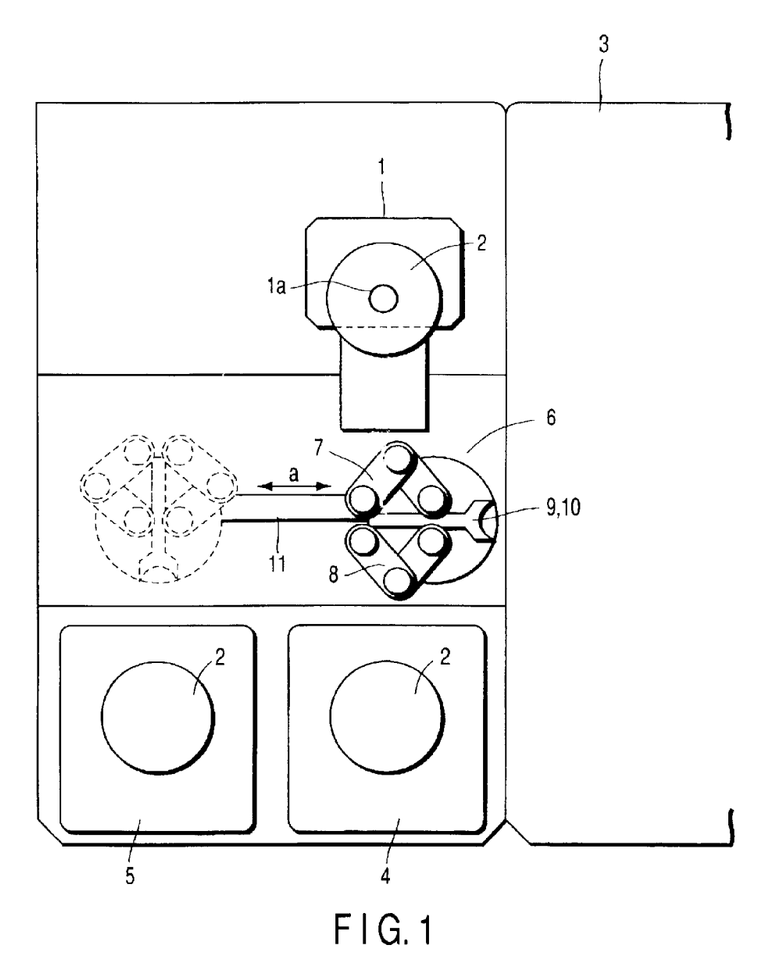
FIG. 1 shows the structure of an aligner to which a semiconductor wafer inspection apparatus according to the first embodiment of the present invention is applied.

FIG. 1 shows the structure of an aligner to which a semiconductor wafer inspection apparatus according to a first embodiment of the present invention is applied. The aligner 1 has a function of aligning semiconductor wafers 2 (hereinafter referred to simply as "wafers") before they are transferred to a defect inspection apparatus main body 3. The defect inspection apparatus main body 3 receives the semiconductor wafers in the aligned state, and inspects the surface or the rear surface of the semiconductor wafers 2 in either a macro fashion or a micro fashion to find various kinds of defects on them.

Two cassettes 4 and 5 are provided to store unexamined wafers 2 and examined wafers 2. A transportation robot 6 is provided between the aligner 1 and the cassettes 4 and 5. The transportation robot 6 serves as a loader section configured to transport wafers 2 from the cassette 4 to the defect inspection apparatus main body 3 by way of the aligner 1.

The transportation robot 6 is provided with two extendable/retractable arms 7 and 8, which are vertically arranged. Hands 9 and 10 are attached to the arms 7 and 8, respectively. Since the hands 9 and 10 overlap each other, they are depicted as one hand. The transportation robot 6 is provided for a driving mechanism 11.

The driving mechanism 11 has a rail extending in parallel to the direction in which the cassettes 4 and 5 are arranged side by side. The driving mechanism 11 drives the transportation robot 6 in the direction indicated by arrow a and brings it to a halt at positions corresponding to the cassettes 4 and 5.

When a wafer 2 is set on the rotatable table 1a, the aligner 1 rotates the wafer 2 at a constant rotating speed and detects the center position of the wafer 2 and the direction in which a notch or an orientation flat is present. Based on the result of this detection, the wafer 2 is aligned.

Figure 2:
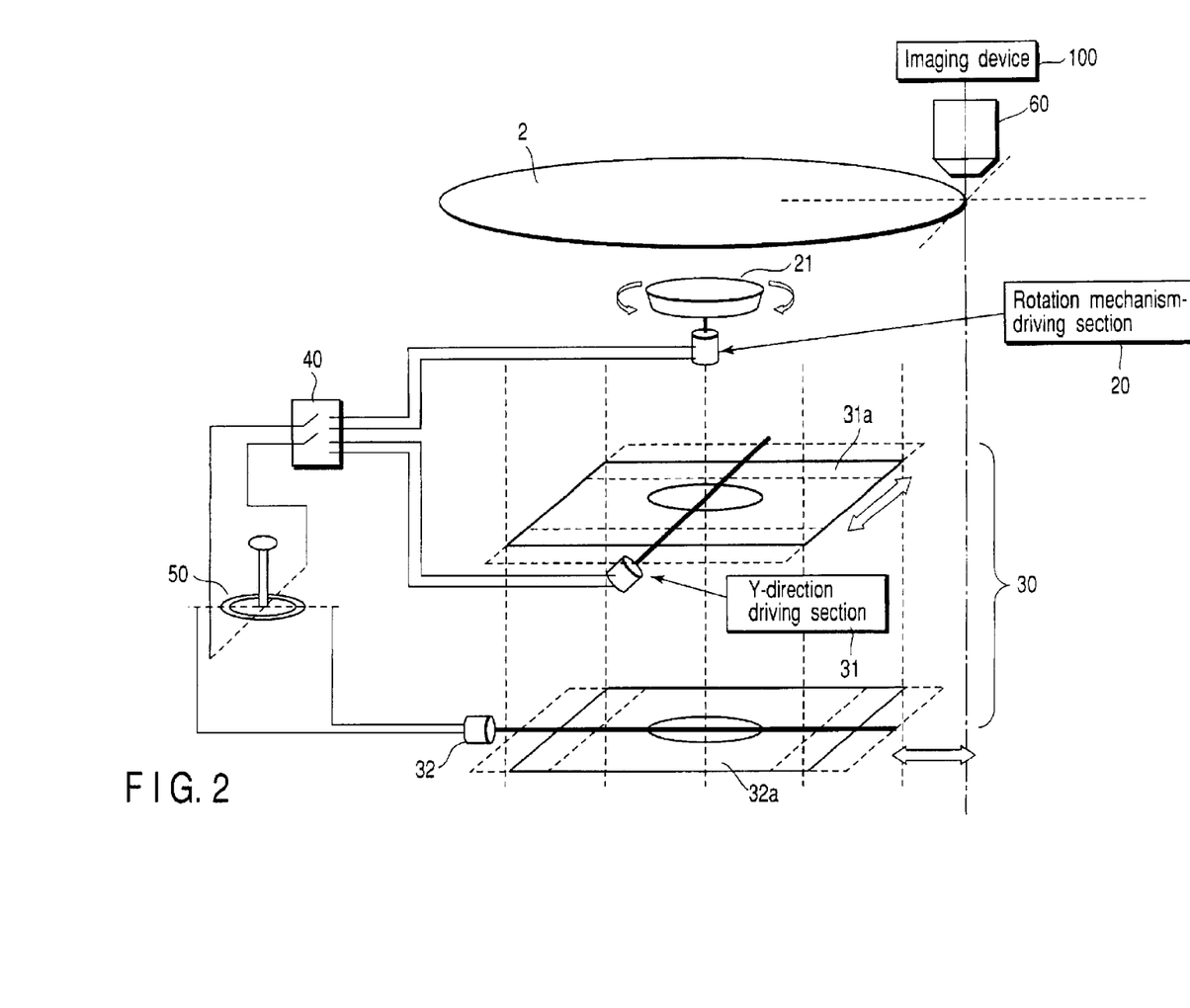
FIG. 2 is a schematic illustration showing the structure of a defect inspection apparatus main body according to the first embodiment of the present invention.

FIG. 2 is a schematic illustration showing the structure of a defect inspection apparatus main body 3 according to the first embodiment of the present invention.

Referring to FIG. 2, a 2-axis movement stage 30 (i.e., an electric stage), which is movable in both an X-axis direction and a Y-axis direction, is made up of a Y-direction movement stage 31a and an X-direction movement stage 32a. The Y-direction movement stage 31a is driven in the Y direction by a Y-direction driving section 31; likewise, the X-direction movement stage 32a is driven in the X direction by an X-direction driving section 32. A rotatable table 21 is located above the 2-axis movement stage 30. The rotatable table 21 holds a wafer thereon by suction and is rotated by a rotation mechanism-driving section 20.

In a micro observation mode, an imaging device 100 captures image data through the use of an objective lens 60 of a microscope. When the edge portion of a wafer is inspected, an edge observation mode is set. In this mode, the Y-direction movement stage 31a and the X-direction movement stage 32a are controlled in such a manner that the edge portion of the wafer sucked and held on the rotatable table 21 comes to the position under the objective lens 60. After the wafer edge portion is adjusted to the position under the objective lens in this manner, the imaging device 100 begins to capture image data. An image of the wafer edge portion obtained with the imaging device 100 is sent to an image processing section where it is subjected to numerical analysis for the calculation of an edge cut amount.

The semiconductor wafer inspection apparatus is operated using the GUI (graphic user interface) shown on an operation panel or the display section of a computer.

An "edge observation"/"ordinary observation" switching device 40 is a switch that allows switching between the rotation mechanism-driving section 20 and the Y-direction driving section 31, which are to be controlled by a pointing device 50. The pointing device 50 is a joy stick (JS), for example. The pointing device 50 controls the position of the 2-axis movement stage 30. The pointing device 50 can also control the rotatable table 21 to determine the rotating direction and speed of the wafer. With this configuration, during the observation of the edge portion (outer circumference) of a wafer, fine adjustment can be made to the wafer position so that the edge portion of the wafer can be located at the position under the objective lens 60, and fine adjustment can be made to the rotating speed to adjust the observation speed.

A description will now be given as to how the semiconductor wafer inspection apparatus of the above structure operates.

Figure 3:
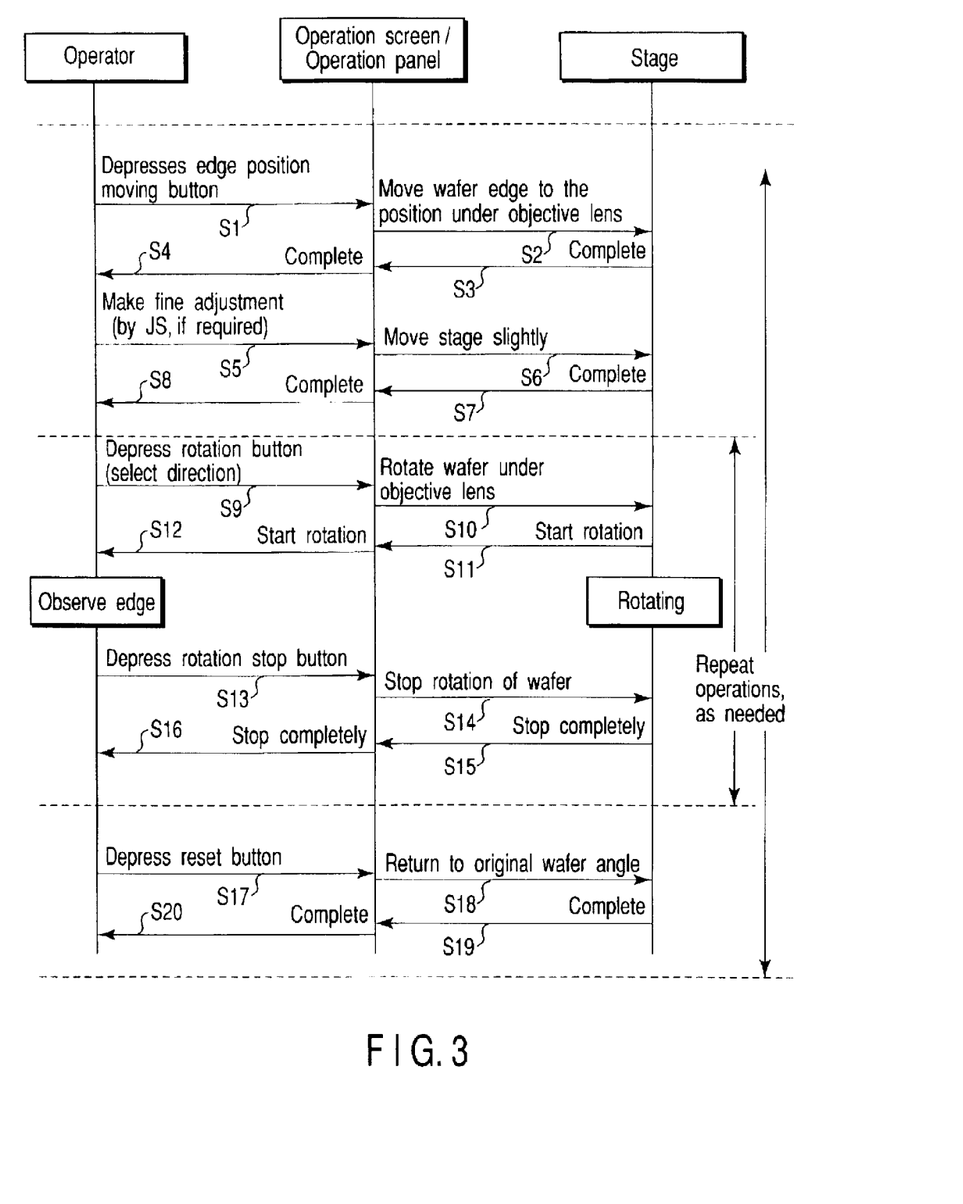
FIG. 3 illustrates how the semiconductor wafer inspection apparatus of the first embodiment of the present invention operates.

FIG. 3 illustrates how the semiconductor wafer inspection apparatus of the first embodiment of the present invention operates. In the description below, reference will be made to the case where the operator first performs ordinary defect inspection of a wafer surface and then performs inspection of a wafer edge portion. First of all, in step S1, the operator depresses an edge moving button provided for the operation panel or an edge position moving button displayed on a screen of a display device. An edge position moving button, a rotation button, a rotation stop button, a rotation/ movement speed switching button, a pointing device, and other operation buttons are displayed on a display device. When one of the operation buttons is depressed, the corresponding operation is performed.

When the edge position moving button is depressed, for example, the X-direction movement stage 32a of the 2-axis movement stage 30 moves in the X direction. As a result, the wafer sucked and held on the rotatable table 21 moves until the edge portion comes to the position under the objective lens 60 in step S2, thereby enabling observation of a detailed image of the wafer edge portion and its neighboring portion. If focusing of the objective lens 60 is executed with the auto focus function enabled during the observation of the wafer edge portion, the wafer edge may move out of the range of the objective lens 60, making the focusing impossible. To prevent this problem, it is preferable to disable the auto focus function during the observation of the wafer edge portion. When the wafer edge portion comes to the position under the objective lens 60, a completion signal is sent from the stage in step S3, and a message indicating this is displayed on the operation screen or operation panel. Then, the operator confirms the image shown on the display device in step S4, operates the pointing device 50, as needed, in step 5, and makes fine adjustment to the 2-axis movement stage 30 in step S6 so that the wafer edge portion entirely comes within the field of view of the objective lens. Thereafter, a completion signal is returned from the Y-direction driving section 31 and the X-direction driving section 32 in step S7, and the operator confirms the image shown on the display device in step 8.

Then, the operator selects the rotating direction by depressing the rotation button in step S9. In response to this selection, rotation mechanism-driving section 20 is driven in step S10, and the wafer 2 on the rotatable state 21 begins to rotate. In response to the rotation of the rotatable stage 21, a rotation start signal is returned from the rotation mechanism-driving section 20 to the operation screen or operation panel in step S11. The rotatable table 21 keeps rotating until the operator depresses the rotation stop button. In response to the rotation of the rotatable table 21, the imaging device 100 captures an image of the edge portion of the wafer 2 located under the objective lens 60 and the display device displays the captured image. In step S12, the operator observes an image of the wafer edge portion displayed on the display device. When the wafer 2 has started rotating or in response to the instruction by the operator, the "edge observation"/"ordinary observation" switching device 40b is operated to select the edge observation mode. In this mode, the rotating speed of the rotatable table 21 can be adjusted by means of the pointing device 50.

Thus, before the observation of the wafer edge portion, the position of the 2-axis movement stage 30 can be controlled by means of the pointing device 50 in such a manner that the observation target of the wafer edge portion comes to the center of the field of view of the objective lens 60. After the start of the observation of the wafer edge portion, the rotating speed of the rotatable table 21 can be controlled by means of the pointing device 50 so that the observation speed becomes optimal to the operator. This control significantly enhances the usability.

When the operator depresses the rotation stop button in step S13 at the end of the observation of the wafer edge portion, a stop signal is supplied to the rotation mechanism-driving section 20 to stop the rotation of the rotatable table 21 (the rotation of the wafer). Thereafter, in step S15, a rotation stop signal is returned from the rotation mechanism-driving section 20. The operator determines whether to rotate the wafer 2 or to stop it. When the operator finds an undesirable rinse cut amount or a defective portion such as a crack, the operator can depress the rotation stop button to stop the rotation of the rotatable table 21 as the need arises. When the table 21 stops, an image of the wafer edge portion is captured by means of the imaging device 100 and image data obtained thereby is analyzed by means of the image processing section. When the wafer edge portion is being observed, image data on the portion being observed is acquired regularly (at predetermined intervals). The image processing section analyzes the rinse cut amount and defects, including the crack and wafer chipping (fragment), and calculates the number of defects, coordinate positions, and sizes of the defects.

An automatic defect classification software is installed in the image processing section. If the rinse cut amount is out of a predetermined value range, or if the defect is determined as a crack or wafer chipping, the wafer 2 is determined as defective. If the image processing section determined that the rinse cut amount is undesirable, the wafer 2 is returned to the resist film removing step. If the image processing section determined that the defect is a crack, the wafer 2 is disposed of since it may crack in subsequent steps.

When the operator determined to end the observation of the wafer edge portion in step S16, the operator depresses the reset button in step S17. In response to the depression of the reset button, the rotation mechanism-driving section 20 is controlled in step S18, and the rotatable table 21 is returned to the angular position it takes before observation (an initial state). To be more specific, the angular position (rotating angle) of the wafer is returned to the original position so that the notch of the wafer 2 sucked and held on the rotatable table 21 comes to the original reference position, e.g., the position of 0°. Thereafter, in step S19, a completion signal is returned from the stage, and in step S20, the operator confirms the image displayed on the display device.

Figure 4A:
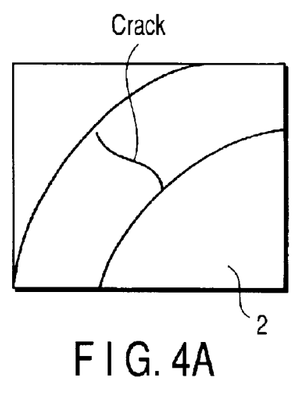
FIGS. 4A and 4B show an example of how a wafer edge portion is displayed in an enlarged scale in the first embodiment of the present invention.
Figure 4B:
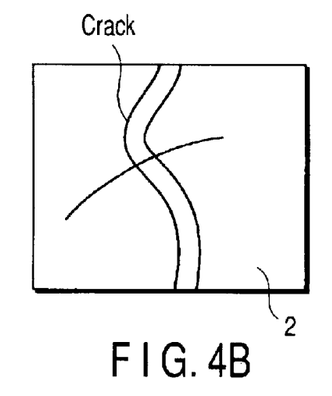

FIGS. 4A and 4B show an example of how a wafer edge portion is displayed in an enlarged scale. If an abnormal portion that is considered to be a crack, for example, shown in FIG. 4A, is found when the wafer edge portion is observed by means of the small-magnification objective lens 60, the objective lens is replaced with a large-magnification one, and enlarged observation is performed in the manner shown in FIG. 4B. The magnification may be changed when the operator finds an abnormal portion during the visual observation through the eyepiece of the microscope or when the automatic defect classification software determines an abnormal portion is contained in the image captured by the imaging device 100.

In the manner described above, the abnormal portion is inspected in an enlarged scale, using the large-magnification objective lens 60. It is therefore possible to easily determine whether the abnormal portion is a defect or not. For example, observation is performed using an objective lens which has small-magnification up to 5× or so. In the case where an abnormal portion is found, the small-magnification objective lens is replaced with an objective lens which has large-magnification of 10×, 20×, 50× or 100× larger than the small-magnification, and detailed defect inspection is performed, with the abnormal portion being enlarged. In the case where the abnormal portion is determined to be a defect, the related defect data and the image data are preferably stored. The defect data and the image data may be used in subsequent inspection.

Figure 5:
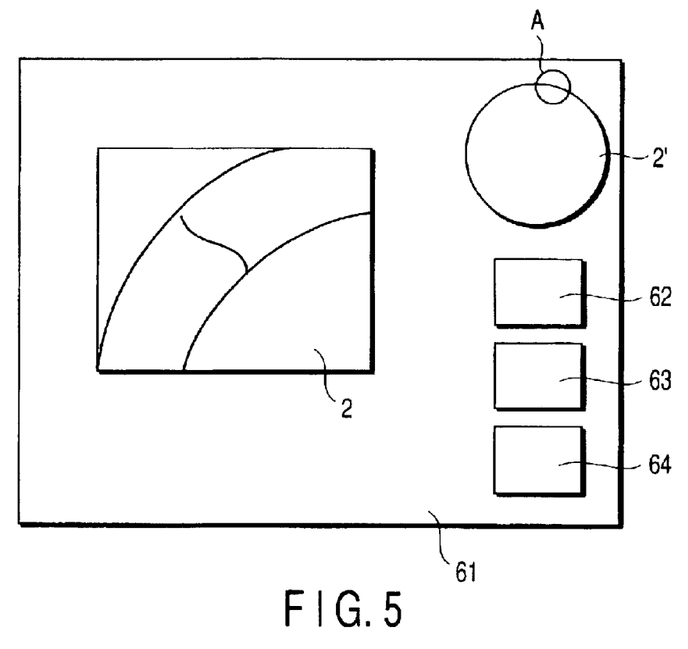
FIG. 5 shows an example displaying a wafer edge portion related to the first embodiment of the present invention.

During observation of a wafer edge portion, the operator sometimes has difficulty in understanding which portion of the entire wafer he or she is observing. As shown in FIG. 5, therefore, the coordinates and the rotating angle of a portion being observed should preferably be detected based on pulse signals provided by the Y-direction driving section 31, X-direction driving section 32 and rotation mechanism-driving section 20. By so doing, the operation screen (operation panel) 61 can display which portion of the wafer 2 is being observed at the present time. For example, a wafer map 2' is displayed on the operation screen, and an observation point A is indicated on the wafer map 2', as shown in FIG. 5. In addition, defects detected by the image processing section may be displayed on the wafer map 2A', with kinds of defect being indicated in colors. When an arbitrary defect position displayed is clicked with a pointer, the defect designated with the pointer may be displayed as an enlarged image. The operation screen 61 shown in FIG. 5 displays not only a wafer image at the observation point A but also the following buttons: a classification button 62 used for classifying the defects according to kinds, a save button 63 used for saving defect images, and a registration button 64 used for registering defect data.

As described above, an alignment mechanism is provided, and the alignment mechanism includes three sensors for detecting a wafer edge. The sensors are on the concentric circle whose radius is the same as the wafer 2 and whose center is the center of rotation of the rotatable table 21 which is disposed on the 2-axis movement stage 30. The alignment mechanism detects how the center of the wafer is shifted on the basis of the coordinate data on the three wafer edge points, and automatically controls the 2-axis movement stage 30 in relation to the rotation of the rotatable table 21 until the center of the wafer 2 becomes the center of rotation. In this manner, even if the semiconductor wafer 2 sucked and held on the rotatable table 21 is shifted from the right position, its position is corrected so that its center becomes the center of rotation. Hence, the wafer edge portion of the semiconductor wafer 2 and its neighboring portion can be accurately observed at all times.

According to the first embodiment, a small-magnification objective lens is replaced with a large-magnification objective lens so as to enable a defective portion to be displayed in an enlarged scale and examined in detail.

It is not necessary to provide an inspection section specially designed for the inspection of a wafer edge. That is, the edge of a wafer on the rotatable table located under the objective lens of a microscope can be observed by making use of the micro observation function of the microscope.

Defects existing on the edge of the circumference of a semiconductor wafer, such as wafer chipping, cracks, and a rinse cut amount, can be detected, and a defective wafer is prevented from being made in the photolithography step executed after the application of photoresist.

Positional information on defects may be displayed on a wafer map, and the kinds of defects may be indicated in different colors. By so doing, it is possible to visually recognize what kind of defect the wafer has, and where it is located.

The present invention is not limited to the first embodiment described above. In the above embodiment, at the start of the edge observation, the 2-axis movement stage moves a semiconductor wafer in the X-Y plane perpendicular to the optical axis direction of the micro observation optical system, until the wafer edge portion comes to the position under the objective lens. Instead of this configuration, the objective lens may be moved to the position located above the wafer edge portion.

The aligner to which the semiconductor wafer inspection apparatus of the second embodiment is applied has a similar structure to that depicted in FIG. 1.

Figure 6:
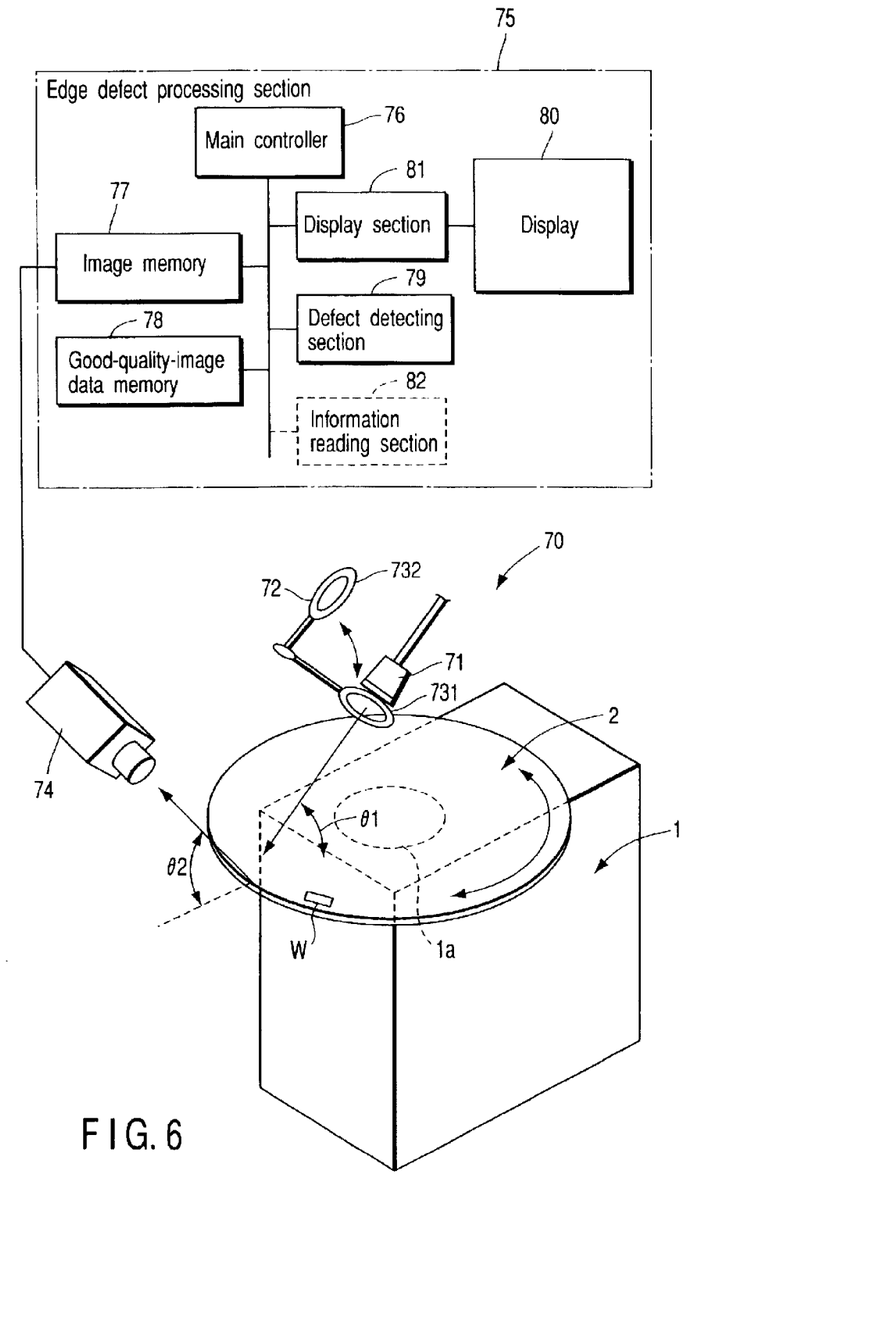
FIG. 6 is a schematic illustration showing the structure of a wafer edge inspection apparatus according to the second embodiment of the present invention.

FIG. 6 is a schematic illustration showing the structure of a wafer edge inspection apparatus according to the second embodiment of the present invention. The aligner 1 described above is provided with a wafer edge inspection apparatus 70, such as that shown in FIG. 6. An illuminating device 71 is located above the aligner 1. Illuminating light emitted from the illuminating device 71 falls on the wafer edge portion of a wafer 2 at a predetermined angle (slantwise illumination). The illuminating angle θ1 of the illuminating device 71 can be set at an arbitrary angle when the illuminating light illuminates the wafer edge portion of the wafer 2 slantwise.

A filter changer 72 is provided in the optical path of the illuminating light emitted from the illuminating device 71. By use of this filter changer 72, either a band-pass filter 731 or a polarizing filter 732 is inserted in the optical path of the illuminating light (removable insertion). When the band-pass filter 731 is inserted in the illuminating optical path, illuminating light having designated wavelengths travels to the wafer edge portion of the wafer 2, thereby enabling interference imaging. When the polarizing filter 732 is inserted in the illuminating path, polarizing imaging is enabled.

An imaging device 74 is disposed above the aligner 1 in such a manner that it is located on the side opposing the illuminating device 71. The imaging device 74 captures images of the wafer edge portion of the wafer 2 when this wafer 2 is rotated at a constant speed by the aligner 1. The imaging device 74 is a one-dimensional CCD (a line sensor camera), a two-dimensional CCD sensor, a time delay camera (a TDI camera), or the like. The imaging device 74 is able to capture images at an arbitrary angle θ2 with respect to the wafer edge portion of the wafer 2. The scaling factor of the imaging device 74 can be arbitrarily determined, thereby enabling selection of an appropriate vertical resolution.

Let us assume that the imaging device 74 is a one-dimensional CCD and is used for continuously capturing images of the wafer edge portion of the wafer 2 rotating at a constant speed in synchronism with the rotating speed of the rotatable table 1a of the aligner 1. In this case, the wafer edge portion is acquired as belt-like image data. Therefore, the horizontal imaging resolution of the imaging device 74 (i.e., the longitudinal resolution of the wafer edge portion) can be varied by changing the rotating speed of the rotatable table 1a.

When the imaging device 74 is moved closer to the wafer 2, the scaling factor increases. Image signals output from the imaging device 74 are supplied to an edge defect processing section 75. The edge defect processing section 75 compares the belt-like image data acquired by the imaging device 74 with image data on a wafer of good quality. Based on this comparison, the edge defect processing section 75 detects a defective portion at the wafer edge portion and displays the related belt-like image data.

To be more specific, the edge defect processing section 75 comprises the following: a main controller 76 such as a CPU; an image memory 77 for which data reading and data writing are enabled under the control of the main controller 76 and which stores image signals from the imaging device 74 as belt-like image data; a good-quality-image data memory 78 which stores image data on the wafer edge portion of a wafer of good quality; a defect detecting section 79 which compares the belt-like image data with the image data on the wafer 2 of good quality and detects a defective portion at the wafer edge portion of the wafer 2; and a display section 81 which causes the belt-like image data to be displayed on a display 80.

The image data on the semiconductor wafer 2 of good quality, which is stored in the good-quality-image data memory 78, is belt-like image data obtained with respect to a wafer 2 which is considered to be a good one in previous inspection. Alternatively, the wafers 2 of one lot are sequentially inspected, and each time a wafer 2 of good quality is determined, the image data of that wafer 2 is used as updating data.

The defect detecting section 79 compares the belt-like image data with image data on a wafer 2 of good quality. Based on the comparison, the defect detecting section 79 determines the kinds of defects at the wafer edge portion of a wafer 2, such as dust, scratches, wafer chipping, cracks, etc., and calculates the number of defects the wafer 2 has, the coordinate positions (X, Y) of the defects, and the areas (sizes) of the defects.

The defect detection section 79 detects an edge cut line width after photoresist is coated on the surface of the wafer 2 in the semiconductor manufacturing process. The edge cut line width is a width by which the photoresist is cut out after dropping a rinse liquid on the wafer edge portion of the wafer 2. The detected edge cut line width is compared with a predetermined threshold value to determine if the edge cut line width is within a normal range. If abnormality is detected, the defect detecting section 79 calculates the coordinate positions (X, Y) and areas.

Figure 7:
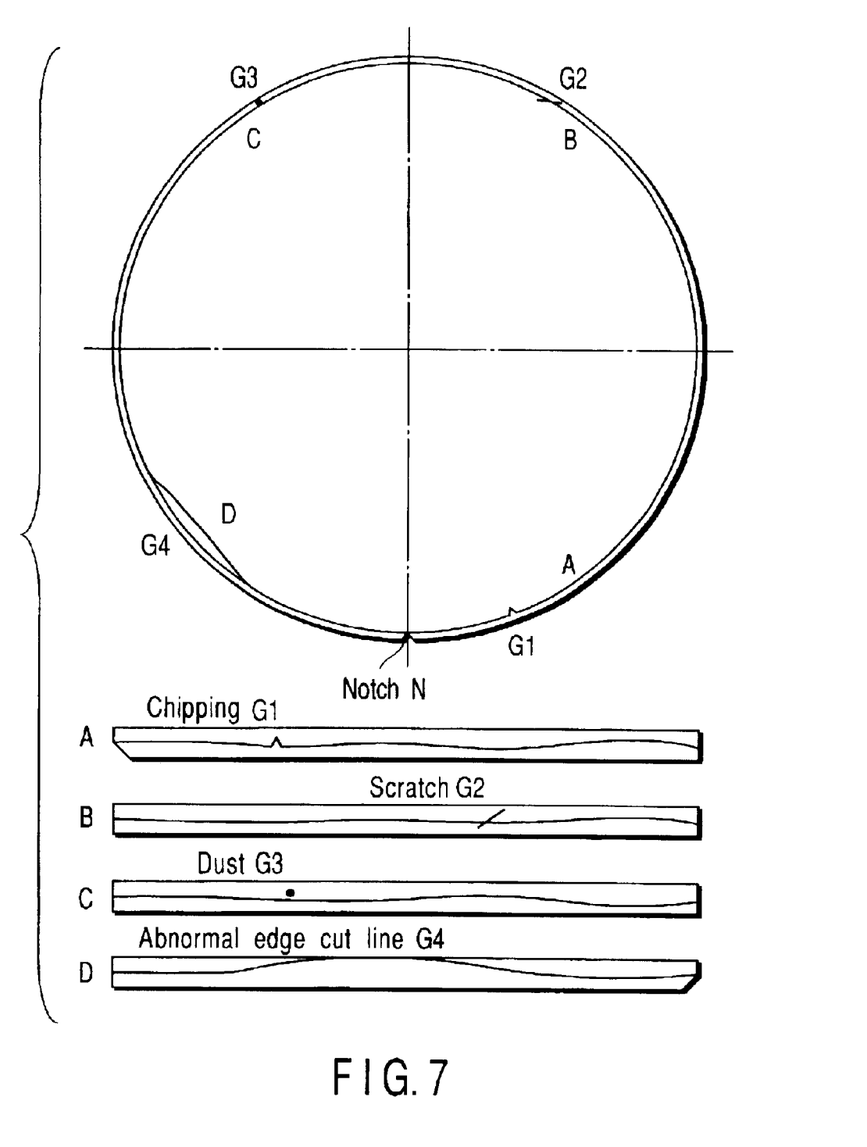
FIG. 7 shows an example of how belt-like image data is displayed in the wafer edge inspection apparatus of the second embodiment of the present invention.

FIG. 7 shows an example of how belt-like image data is displayed in the wafer edge inspection apparatus. The display section 81 divides belt-like image data into a plurality of pieces, for example four image data pieces A, B, C and D corresponding to 90° of the wafer 2, as shown in FIG. 7. These image data pieces A, B, C and D are displayed on the display 80.

G1 denotes chipping in image data piece A, G2 denotes a scratch in image data piece B, G3 denotes a dust particle in image data piece C, and G4 denotes an abnormal portion of an edge cut line width in image data piece D.

The display section 81 has a function of laying out the belt-like image data obtained by the line sensor camera on the screen of a wafer map in such a manner that it forms a circular shape and displaying it on the display 80, as shown in FIG. 7. In this image processing, the four image data pieces A, B, C and D form one circular image.

Figure 8:
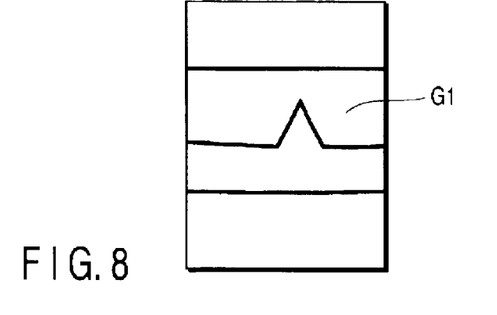
FIG. 8 shows an example of how a defective portion image is displayed in an enlarged scale in the second embodiment of the present invention.

When one of the defective portions G1-G4 is clicked after moving a pointer thereto on the wafer map displayed on the display 80, the display section 81 causes an enlarged image of the corresponding defective portion to be displayed on the display 80, as shown in FIG. 8.

The display section 81 has a function of classifying and displaying the defective portions G1 to G4 in different colors according to their kinds, when the belt-like image data (image data pieces A, B, C and D) is displayed on the display 80.

Figure 9:
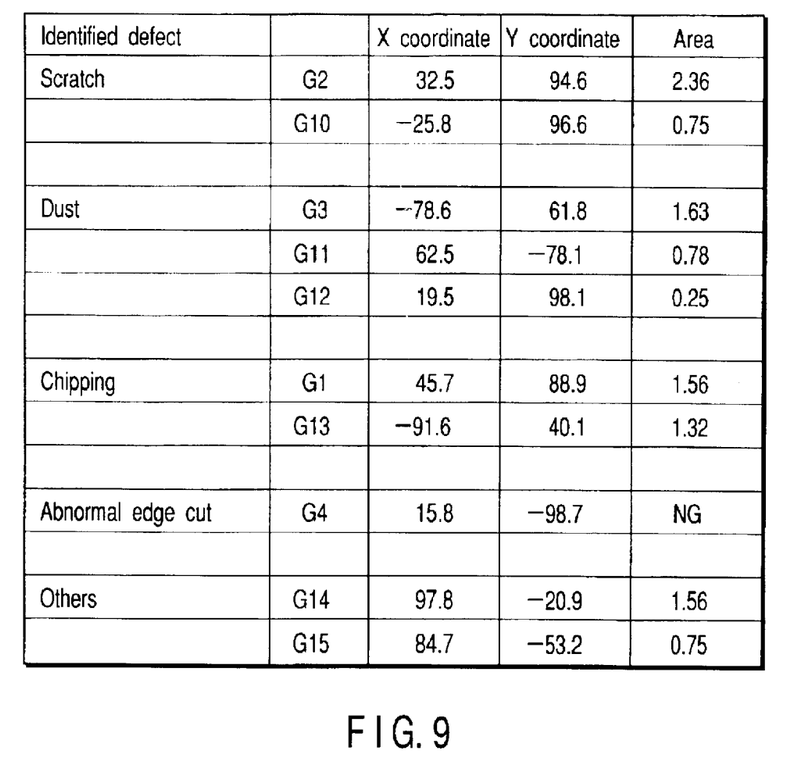
FIG. 9 is a schematic diagram showing coordinate positions and areas of defective portions, which are calculated by a defect detector according to the second embodiment of the present invention.

The display section 81 displays not only belt-like image data (image data pieces A, B, C and D) but also results of determination made by the defect detecting section 79. Examples of defects at the wafer edge portion of the semiconductor wafer 2 include a scratch, dust, chipping (wafer chipping), an abnormal edge cut line width, crack, etc., and examples of the results of determination include coordinate positions (X, Y) of the defects, areas of them, etc.

A description will now be given as to how the wafer edge inspection apparatus of the above configuration operates.

When a wafer 2 is set, the aligner 1 rotates the wafer 2 at a constant rotating speed, and detects the coordinates of three points on the edge of the wafer 2 by a edge sensor. Based on the edge coordinate data on points, the center position of the wafer 2 and the direction of the notch are detected. The semiconductor wafer 2 is aligned on the basis of the results of detection.

Simultaneous with this, the illuminating device 71 illuminates the wafer edge portion of the semiconductor wafer 2 rotating at a constant speed. The illumination angle is θ1.

The imaging device 74 captures images of the light reflected by the wafer edge portion of the wafer 2 rotated by the aligner 1 at a constant rotating speed. The images are captured at arbitrary angle θ2, which is determined relative to the wafer edge portion of the wafer 2. The image signals are output and stored in the image memory 77 of the edge defect processing section 75 as belt-like image data on the wafer edge portion of the wafer.

The defect detecting section 79 of the edge defect processing section 75 compares the captured image data with image data on a good-quality wafer. Based on this comparison, the defect detecting section 79 calculates the coordinate positions (X, Y) and areas of the defects at the wafer edge portion, such as dust, a scratch, chipping (wafer chipping), a crack, an abnormal edge cut line width, etc.

The display section 81 divides the captured belt-like image data stored in the image memory 77 into pieces, as shown in FIG. 7. For example, four image data pieces A, B, C and D are prepared (all four pieces are considered to constitute a circle, so that each of the four pieces corresponds to 90°, for example). These divided image data pieces A, B, C and D are displayed on the display 80. Simultaneous with this, the display section 81 lays out the belt-like image data in such a manner that the laid-out image data forms a circle in conformity with the circular shape of the semiconductor wafer 2. The resultant circular image data is shown on the display 80.

As shown in FIG. 7, the circular image data is displayed in the upper portion of the screen of the display 80, and the four belt-like image data pieces A, B, C and D are displayed in the lower portion so that they are arranged in the vertical direction. Reference symbols G1 to G4 are indicated in both the circular image and the belt-like divided images (G1: chipping, G2: scratch, G3: dust, G4: abnormal portion of edge cut line width).

In the screen portion of the display 80 where the belt-like image data (image data pieces A, B, C and D) is displayed, the display section 81 shows the defective portions G1 to G4 in different colors according to their kinds.

The display section 81 displays not only belt-like image data (image data pieces A, B, C and D) but also results of determination made by the defect detecting section 79. Examples of defects at the wafer edge portion of the wafer 2 include a scratch, dust, chipping (wafer chipping), an abnormal edge cut line width, crack, etc., and examples of the results of determination include coordinate positions (X, Y) of the defects, areas of them, etc.

In the second embodiment described above, the imaging device 74 captures images of the wafer edge portion of the wafer 2 when this wafer 2 is rotated at a constant speed by the aligner 1. The captured belt-like image data is compared with image data on a good-quality wafer, for the defect inspection of the wafer edge portion of the semiconductor wafer 2. Simultaneous with this defect inspection, the belt-like image data is displayed as divided image data pieces A, B, C and D, and as circularly laid-out image data. Therefore, defects at the wafer edge portion of the circumference of the semiconductor wafer 1 can be detected, including dust, a scratch, chipping (wafer chipping), a crack, and an abnormal portion of an edge cut line width.

Because of the defect detection described above, one of the causes of defective wafers being manufactured can be reliably detected when the processing of the steps that follows the application of a thin photoresist film is executed. In addition, since the horizontal imaging resolution can be varied by changing the rotating speed of the aligner 1, the resolution in the longitudinal direction of the wafer edge portion can be improved. As a result, distortion-free image data can be acquired, and defects can be detected with high accuracy.

When the aligner 1 performs an alignment operation to transport a wafer 2 to the defect inspection apparatus main body 3, the aligner 1 rotates that wafer 2 at a constant speed. This rotation is utilized in the defect inspection performed for the wafer edge portion of the wafer 2. Therefore, the inspection of a wafer edge can be performed without employing a dedicated inspection apparatus, and what is required is a simple structure wherein the illuminating device 71, the imaging device 74 and the edge defect processing section 75 are merely added to the existing aligner 1.

Furthermore, both the belt-like image data and the circularly laid-out image data are displayed. Thanks to this feature, it is possible to visually recognize where defects G1 to G4 (e.g., dust, a scratch, wafer chipping, a crack, an abnormal portion of a edge cut line width) are located on the actual semiconductor wafer 2.

Information on the wafer 2, such as a wafer identification number W (a wafer ID), is attached to the wafer edge portion of the semiconductor wafer 2. The identification number W is attached at the predetermined position on the wafer edge portion. The identification number W is character information "AEO21", for example.

To recognize the identification number W, the image device 74 is moved to the position where the identification number W is attached. Image signals output from the imaging device 74 are subjected to image processing executed by an information reading section 82 additionally provided for the edge defect processing section 75 shown in FIG. 6. Based on this image processing, the identification number of the semiconductor wafer 2 attached to the wafer edge portion is recognized as characters or letters.

There may be a case where the wafer edge portion of the semiconductor wafer 2 is covered with a thin film. In this case, the identification number W of the semiconductor wafer 2 is not recognized as characters or letters. To solve this problem, a filter having a predetermined wavelength is provided for either the illuminating device 71 or the imaging device 74. The filter enables the identification number W to be recognized as characters or letters, despite the thin film covering the wafer wedge portion of the semiconductor wafer 2.

Defects may be displayed together with reference symbols G1 to G4 attached thereto or in different colors according to their kinds. Where the defects are displayed in this manner, the positions and kinds of the defects can be correctly identified.

The actual image processing required for displaying the circularly laid out image data is simply a matter of pasting the four image data pieces A, B, C and D to one another. In other words, no complicated image processing is needed.

As the defects G1 to G4 on the wafer edge portion of the semiconductor wafer 2, dust, a scratch, wafer chipping, a crack, an abnormal portion of a edge cut line width etc. are displayed, and they are displayed together with their coordinate positions (X, Y) and areas. This enables easy understanding of the states of the defects G1 to G4. In addition, the defects G1 to G4 can be inspected in detail by displaying enlarged images of them on the screen of the display 80.

Observation based on interference imaging can be performed by inserting the band-pass filter 731 in the illumination path by means of the filter changer 72. Likewise, observation based on polarized imaging can be performed by inserting the polarizing filter 732 in the illumination path by means of the filter changer 72.

Figure 10:
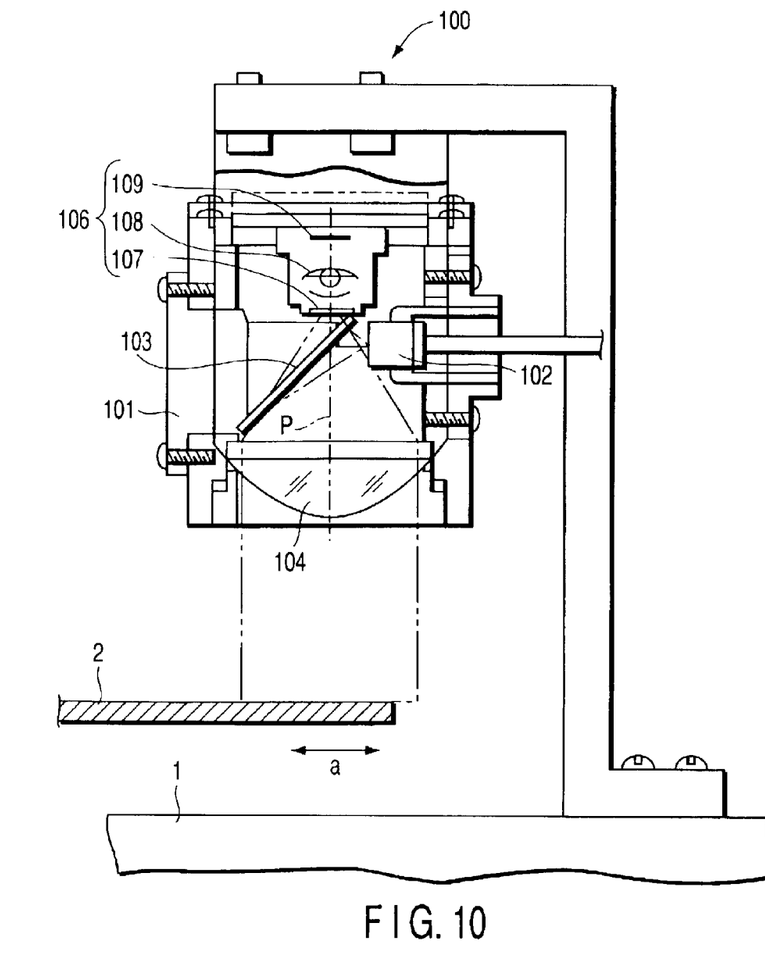
FIG. 10 shows the structure of an edge defect inspection apparatus according to the third embodiment of the present invention.

FIG. 10 shows the structure of an edge defect inspection apparatus according to the third embodiment of the present invention. The edge defect inspection apparatus 100 is featured by employing an incident telecentric illuminating/image formation optical system. A sensor casing 101 is tubular.

The light source is a light emitting diode (LED) 102. The LED 102 emits LED light and is provided on the side face of the sensor casing 101.

A half mirror 103 is provided slantwise inside the sensor casing 101. The half mirror 103 is an optical path-splitting element. It reflects the LED light emitted from the LED 102 so that the reflected LED light travels toward a telecentric lens 104. It also allows transmission of reflected light reflected by a semiconductor wafer 2 and condensed by the telecentric lens 104.

The telecentric lens 104 functions as a collimating lens for collimating the LED light emitted from the LED 102 and irradiating the wafer edge portion of the semiconductor wafer 2 with the collimated LED light. The telecentric lens 104 also functions as a focusing lens for focusing the LED light reflected by the semiconductor wafer 2.

An image sensor 106 is on the optical axis P of the telecentric lens 104 and located on the rear focus side of the lens 104. The image sensor 106 includes a diaphragm 107, a relay image formation lens 108 and a two-dimensional imaging element 109.

The two-dimensional imaging element 109 includes a plurality of solid-state imaging elements (CCD) that are arranged in rows and columns in a two-dimensional plane. The image sensor 106 functions as a line sensor camera by using image data which are included in two-dimensional image signals acquired by the two dimensional imaging element 109 and which correspond to one line or a number of lines.

The edge defect inspection apparatus 100 is located above the wafer edge portion of the wafer 2 at a position where it does not become an obstacle to the transportation or conveyance of the wafer 2. The edge defect processing section 75 shown in FIG. 6 is connected to the output terminal of the image sensor 106.

As in the second embodiment, the edge defect inspection apparatus 100 of the third embodiment captures images of the wafer edge portion of the semiconductor wafer 2 rotating at a constant speed by the aligner 1. In synchronism with the constant rotating speed of the aligner 1, the two-dimensional imaging element 109 of the image sensor 106 captures images of the wafer edge portion of the semiconductor wafer 2. As a result, the belt-like image data of the wafer edge portion, such as that shown in FIG. 7, is acquired. Since the image processing by the edge defect processing section 75 is similar to the image processing performed in the second embodiment, a detailed description of it will be omitted.

Like the second embodiment, the third embodiment acquires images of the wafer edge portion of the rotating wafer 2 with the image sensor 106, compares the resultant belt-like image data with image data on a good product, and inspects the wafer edge portion of the semiconductor wafer 2 on the basis of the comparison.

The third embodiment produces advantages similar to those of the second embodiment. In addition, the LED 102, the telecentric lens 104 and the image sensor 106 are arranged close to the half mirror 103, so that the edge defect inspection apparatus 100 is small as a whole. Hence, the edge defect inspection apparatus 100 can be easily applied to the aligner of a manufacturing apparatus, such as an inspection apparatus which performs surface defect detection or pattern shape measurement with respect to a semiconductor wafer 2 supplied in a semiconductor manufacturing process, an exposure apparatus, or the like.

The present invention is not limited to the second or third embodiment. For example, data can be displayed on the screen of the display 80 in a modified manner, as described below.

Figure 11:
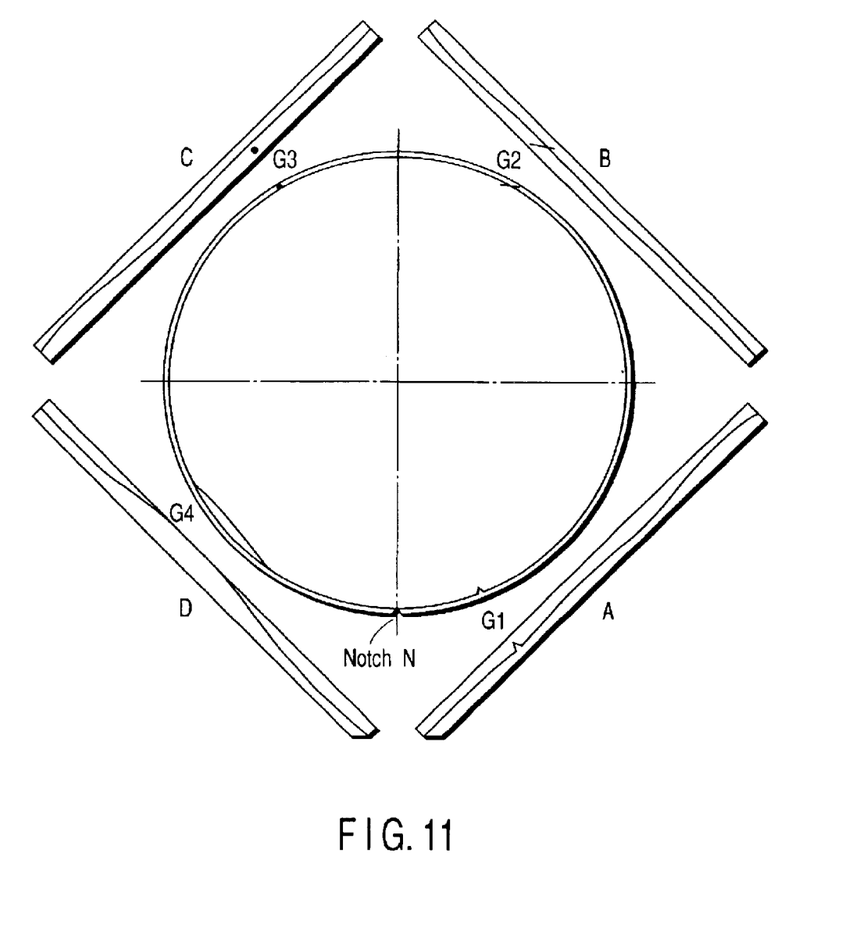
FIG. 11 shows a modification of how the belt-like image data is displayed in the wafer edge inspection apparatus of the third embodiment of the present invention.
Figure 12:
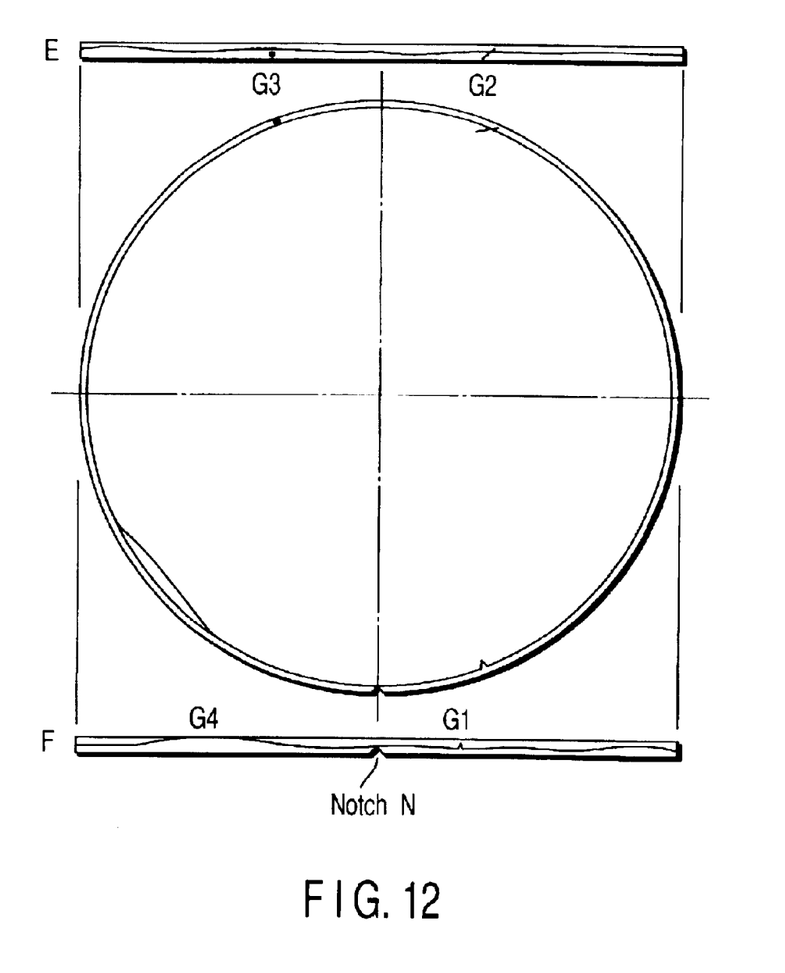
FIG. 12 shows a modification of how the belt-like image data is displayed in the wafer edge inspection apparatus of the third embodiment of the present invention.

FIGS. 11 and 12 show modifications of how belt-like image data is displayed in the wafer edge inspection apparatus. In the display examples shown in FIG. 11, image data pieces A, B, C and D are displayed along the outer circumference of circularly laid-out image data. In other words, the image data pieces A, B, C and D are displayed so that each may correspond to 90° of the circular image data. In this manner, the positional relationships between the image data and the divided image data pieces are indicated.

In the display example shown in FIG. 12, image data pieces E and F are displayed above and under the circularly laid-out image data. In other words, the divided image data pieces E and F are displayed so that each may correspond to 180° of the circular image data. In this manner, the positional relationships between the image data and the divided image data pieces are indicated. In the display example, the image data is divided into two pieces E and F each corresponding to 180°. The angle based on which the circular image data is divided can be determined arbitrarily.

When an enlarged image of a defect (e.g., defect G1) is displayed in response to a click operation by the operator, a zoom function may be utilized. That is, the scaling factor may be changed continuously. In addition, the positions of defects G1 to G4 may be detected using the notch N or orientation flat of the semiconductor wafer 2 as a reference position. In this case, the positions of defects G1 to G4 are calculated and displayed as angles determined in relation to that reference position. Further, part of the belt-like image data is displayed on the display 80, and the displayed area may be varied in response to the operator's operation, for scroll display.

The semiconductor wafer apparatus can be provided for various types of manufacturing apparatuses which rotate wafers 2 at a constant speed. Needless to say, the present invention is not limited to the field of manufacturing semiconductor devices; it may be applied to any type of apparatus that is used for inspection or observation of the outer circumference of a circular object.

The present invention is not limited to the embodiments described above, and may be modified in various ways without departing from the spirit and scope of the invention.

According to the present invention, it is possible to provide a semiconductor wafer inspection apparatus that enables the outer circumference portion of a semiconductor wafer to be easily inspected in a short time in a semiconductor device manufacturing/inspecting step.

In other words, according to the present invention, the edge portion of the semiconductor wafer and its neighboring portions can be smoothly observed by use of a micro observation optical system. Therefore, the semiconductor manufacturing apparatus can execute an inspection step with high efficiency. In addition, since the edge portion can be observed easily and a smooth operation enabled, the productivity in the semiconductor inspection process can be increased.

Furthermore, the present invention enables defect determination for the circumference of the edge portion of the semiconductor wafer.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A semiconductor wafer inspection apparatus comprising:

a rotatable table on which a semiconductor wafer is held by suction;

an illuminating device which illuminates at least an edge portion of the semiconductor wafer held on the rotatable table;

an imaging device which captures an image of the edge portion of the semiconductor wafer by light from a surface of the edge portion when the edge portion is illuminated by the illuminating device;

an image processing device which detects at least one of an edge cut line width and a crack on the surface of the edge portion by acquiring the image of the edge portion which is captured by the imaging device; and a display section which displays an image of the edge portion subjected to image processing by the image processing device;

wherein the imaging device captures a continuous one-dimensional image of the edge portion of the semiconductor wafer when the rotatable table is being rotated, and the image processing device acquires the captured image of the edge portion of the semiconductor wafer as a belt-like image.

2. A semiconductor water inspection apparatus comprising:

a rotatable table on which a semiconductor wafer is held by suction;

an illuminating device which illuminates at least an edge portion of the semiconductor wafer held on the rotatable table;

an imaging device which captures an image of the edge portion of the semiconductor wafer when the edge portion is illuminated by the illuminating device;

an image processing device which detects at least one of an edge cut amount and a crack by acquiring the image of the edge portion which is captured by the imaging device; and a display section which displays an image of the edge portion subjected to image processing by the image processing device;

wherein the imaging device captures a continuous one-dimensional image of the edge portion of the semiconductor wafer when the rotatable table is being rotated, and the image processing device acquires the captured image of the edge portion of the semiconductor wafer as a beat-like edge image.

3. A semiconductor wafer inspection apparatus according to claim 2, wherein the image processing device causes the display section to display a wafer map of the semiconductor wafer and to display the belt-like edge image in a divided fashion in correspondence to circumferential positions of the wafer map.

4. A semiconductor wafer inspection apparatus according to claim 2, wherein tin image processing device causes the display section to display the belt-like edge image such that the belt-like edge image overlaps with peripheral portions of a wafer map of the semiconductor wafer, and an enlarged image of a defect is displayed when the defect displayed on the edge image is clicked by means of a pointer.

5. A semiconductor wafer inspection apparatus according to claim 3, wherein the image processing device causes the display section to display the belt-like edge image such that the belt-like edge image overlaps with peripheral portions of the wafer map of the semiconductor wafer, and an enlarged image of a defect is displayed when the defect displayed on the edge image is clicked by means of a pointer.

* * * * *